United States Patent [19]
Miao et al.

[11] Patent Number: 6,093,723
[45] Date of Patent: Jul. 25, 2000

[54] 4-SUBSTITUTED BETA-CARBOLINES AND ANALOGS THEREOF

[75] Inventors: Clara K Miao, Easton; Ian F. Potocki; Roger J. Snow, both of Danbury; Karl D. Hargrave, Brookfield; Thomas P. Parks, Ridgefield, all of Conn.

[73] Assignee: Boehringer Ingelheim Pharmaceuticals, Inc., Ridgefield, Conn.

[21] Appl. No.: 08/908,211

[22] Filed: Aug. 8, 1997

Related U.S. Application Data

[60] Provisional application No. 60/023,650, Aug. 9, 1996.

[51] Int. Cl.$^7$ .................. A61K 31/44; A61K 31/535; C07D 471/04
[52] U.S. Cl. .................. 514/292; 514/212; 514/228.2; 514/232.8; 514/249; 514/254; 514/291; 540/483; 540/597; 544/60; 544/126; 544/353; 544/405; 546/80; 546/85; 546/86; 546/87; 546/89
[58] Field of Search ............... 546/85, 87, 86, 546/89, 80; 514/292, 291, 212, 228.2, 232.8, 249, 254; 540/483, 597; 544/60, 126, 353, 405

[56] References Cited

U.S. PATENT DOCUMENTS

| | | | |
|---|---|---|---|
| 4,731,358 | 3/1988 | Huth | 514/81 |
| 5,010,077 | 4/1991 | Braestrup et al. | 514/228.8 |
| 5,294,443 | 3/1994 | Lipsky et al. | 424/195.1 |
| 5,359,078 | 10/1994 | Kohn | 548/255 |
| 5,633,277 | 5/1997 | Connell | 514/428 |

FOREIGN PATENT DOCUMENTS

| | | |
|---|---|---|
| 3240514 A1 | 5/1984 | Germany . |
| 7-112918 | 5/1995 | Japan . |
| 859889 | 8/1981 | U.S.S.R. . |
| WO 96/22989 | 8/1996 | WIPO . |

OTHER PUBLICATIONS

Bracher F et al. Tetrahedron 50(43), 12329–36, 1994.
Murakami Y et al. Chem. Pharm. Bull. 39(9), 2189–95, 1991.
Arbain D et al. Aust. J. Chem. 43(2), 433–7, 1990.
Koike K et al. Org. Magn. Reson. 22 (7), 471–3, 1984.
Ablov AV et al. Kinet. Katal. 17(5), 1331–2, 1976.
Bourguignon–Zylber N et al. Chim. Ther. 5 (6), 396–400, 1970.
Vember PA et al. Khim. Prir. Soedin. 3(4), 249–53, 1967.
Sharipov IN et al. Izv. Akad. Nauk Mold. SSR, Ser. Biol. Khim. Nauk (1), 86–8, 1979.
Bracher, F., and Hildebrand, D., "1,9–Dimetalated β–Carbolines. Versatile Building Blocks for the Total Synthesis of Alkaloids," *Tetrahedron* 50(43):12329–12336 (1994).
Bracher, F., and Hildebrand, D., "β–Carboline alkaloids. 7. Versatile building blocks for the total synthesis of alkaloids," *Chem. Abstr.* 122:56289f (Jan. 1995).
Bourguignon–Zylber, N., and Polonsky, J., "Études des constituants des écorces et du bois de *Perriera madagascariensis*. Isolement et structure d'un nouvel alcaloïde indolique et d'un nouveau quassinoïde," *Chim. Ther.* V(6):396–400 (1971).
Bourguignon–Zylber, N., and Polonsky, J., "Constituents of *Perriera madagascariensis* bark and wood. Isolation and structure of a new indole alkaloid and a new quassinoid compound," *Chem. Abstr.* 75:31236j (1971).
Cain, M., et al., "Dichlorodicyanoquinone Oxidations in the Indole Area. Synthesis of Crenatine," *J. Org. Chem.* 47:4933–4936 (1982).
Chung, S.C., et al., "Inhibition by SK&F 96365 of $Ca^{2+}$ current, IL–2 production and activation in T lymphocytes," *Br. J. Pharmacol.* 113:861–868 (1994).
Efremova, T.M., et al., "Carbolines. VII. 1–Methyl–4–hetarylmethyl–β–carbolines," *Khim. Geterotsikl. Soedin.* 10:1382–1387 (1974).
Efremova, T.M., et al., "Carbolines. VII. 1–Methyl–4–hetarylmethyl–β–carbolines," *Chemistry of Heterocyclic Compounds* 10(10):1210–1214 (1974) (English–language translation, dated Mar. 1976).
Efremova, T.M., et al., "Carbolines. VII.1–Methyl–4–heteroarylmethyl–β–carbolines," *Chem. Abstr.* 82:43215j (1975).
Fukada, N., et al., "Synthetic Studies in the β–Carboline Area. New Entry into 4–Substituted and 3,4–Disubstituted β–Carbolines," *Tetrahedron Lett.* 26(18):2139–2142 (1985).

(List continued on next page.)

*Primary Examiner*—Evelyn Mei Huang
*Attorney, Agent, or Firm*—Robert P. Raymond; Anthony P. Bottino; Alan R. Stempel

[57] ABSTRACT

This invention relates to 4-substituted β-carbolines and β-carboline analogs that inhibit $Ca^{+2}$ influx and interleukin-2 (IL-2) production. The 4-substituted β-carbolines and β-carboline analogs of this invention are represented by formula (I):

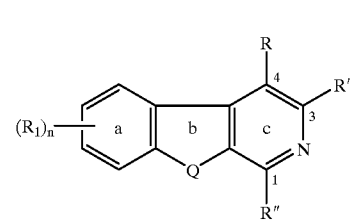

(I)

wherein Q, n, R, R', R" and $R_1$–$R_4$ are as defined herein. This invention also relates to methods for producing β-carbolines. Because of their selective immunomodulating properties, the compounds and pharmaceutical compositions of this invention are particularly well suited for preventing and treating immune disorders, including autoimmune disease, inflammatory disease, organ transplant rejection and other disorders associated with IL-2 mediated immune response.

24 Claims, No Drawings

OTHER PUBLICATIONS

Hagen, T.J., et al., "DDQ Oxidations in the Indole Area. Synthesis of 4–Alkoxy–β–carbolines Including the Natural Products Crenatine and 1–Methoxycanthin–6–one," *J. Org. Chem.* 54:2170–2178 (1989).

Hagen, T.J., et al., "DDQ oxidations in the indole area. Synthesis of 4–alkoxy–β–carbolines including the natural products crenatine and 1–methoxycanthin–6–one," *Chem. Abstr.* 110:193169h (1989).

Haider, N., and van der Plas, H.C., "Intramolecular Diels–Alder Reactions of Pyrazines with Alkynylphenyl Moieties as Side–Chain Dienophiles," *Tetrahedron* 46(10):3641–3650 (1990).

Hiemstra, H.C., et al., "Models of Folate Coenzymes—VIII. An Approach to Yohimbane Alkaloids via Carbon–Fragment Transfer from $N^5,N^{10}$–Methylenetetrahydrofolate Models," *Tetrahedron* 39(23):3981–3986 (1983).

Holt, E.M., et al., "Crystal and molecular structure of crenatine carbonate," *J. Crystallogr. Spectrosc. Res.* 20(3):261–264 (1990).

Holt, E.M., et al., "Crystal and molecular structure of crenatine carbonate," *Chem. Abstr.* 113:172401z (1990).

Jy, W., et al., "Role of $Ca^{2+}$ in the regulation of hormone receptor exposure during lymphocyte activation," *Biochim. Biophys. Acta* 983:153–160 (1989).

Kametani, T., et al., "Nitrenes. Part III. The Reaction of 4–(2–Nitrophenyl)pyridine Derivatives with Triethyl Phosphite," *J. Chem. Soc.* (C)(1):138–140 (1969).

Kametani, T., et al., "Nitrenes. III. Reactions of 4–(2–nitropheyl)–pyridine derivatives with triethyl phosphite," *Chem. Abstr.* 70:47241q (1969).

Khabarov, A.A., and Khabarova, L.P., "Quantitative determination of 1–methyl–4–(N–methyl–1–pyrrolidyl)–β–carboline hydrochloride," *Chem. Abstr.* 96:210151h (1982).

Kohda, K., et al., "Analysis and Distribution of Alkaloids in *Picrasma quassioides,*" *Shoyakugaku Zasshi* 44(4):298–303 (1990).

Kohda, K., et al., "Analysis and distribution of alkaloids in *Picrasma quassioides,*" *Chem. Abstr.* 115:57276s (1991).

Komissarov, I.V., et al., "Synthesis and pharmacological properties of harman and harmine derivatives," *Khim.–Farm. Zh.* 11(5):93–97 (1977).

Komissarov, I.V., et al., "Synthesis and pharmacological properties of harman and harmine derivatives," *Chem. Abstr.* 88:44860b (1978).

Kuchkova, K.I., et al., "Carbolines. I. 1,4–Disubstituted β–Carbolines," *Chemistry of Heterocyclic Compounds* 6(2):182–186 (1970) (English–language translation, dated Jan. 1973).

Kuchkova, K.I., et al., "Carbolines. I. 1,4–Disubstituted β–carbolines," *Chem. Abstr.* 72:121397e (1970).

Kuchkova, K.I., et al., "Carbolines. VIII. α–Carboline compounds from oximes of β–(indol–3–yl) ketones," *Khim. Geterotsikl. Soedin.* 3:386–391 (1976).

Kuchkova, K.I., et al., "Carbolines. VIII. α–Carboline compounds from oximes of β–(indol–3–yl) ketones," *Chem. Abstr.* 85:32897u (1976).

Leete, E., "Biomimetic Synthesis of Brevicolline from Tryptophan, Acetaldehyde, and N–Methyl–$\Delta^1$–pyrrolinium Acetate," *J. Chem. Soc., Chem. Commun.* 18821–822 (1979).

Leete, E., "Biomimetic synthesis of brevicolline from tryptophan, acetaldehyde, and N–methyl–$\Delta^1$–pyrrolinium acetate," *Chem. Abstr.* 92:129163j (1980).

Mazur, G., and Frydecka, I., "Interleukin–2 (IL–2) and interleukin–2 receptor (IL–2R) in normals and in various disorders," *Acta Haematologica Polonica* 24(4):307–313 (1993).

Müller, W., et al., "Ein einfacher Zugang zu 1,4–disubstituierten β–Carbolinderivaten. Die Totalsynthese des $N^a$–Methyl–brevicollins," *Angew. Chem.* 87(10):385–386 (1975).

Mueller, W., et al., "Simple access to 1,4–disubstituted β–carboline derivatives. Total synthesis of $N^a$–methylbrevicolline," *Chem. Abstr.* 83:114712c (1975).

Murakami, Y., et al.,"Synthetic Studies of Indoles and Related Compounds. XXVII. A New Synthesis of Crenatine from Ethyl Indole–2–carboxylate," *Chem. Pharm. Bull.* 39(9):2189–2195 (1991).

Murakami, Y., et al.,"Synthetic studies of indoles and related compounds. XXVII. A new synthesis of crenatine from ethyl indole–2–carboxylate," *Chem. Abstr.* 116:41819f (1992).

Neef, G., et al., "Synthesis of 4–Substituted β–Carbolines," *Heterocycles* 20(7):1295–1313 (1983).

Neef, G., et al., "Synthesis of 4–substituted β–carbolines," *Chem. Abstr.* 99:194831j (1983).

Ohmoto, T., and Koike, K., "Studies on the Alkaloids from *Picrasma quassioides* Bennet. V. Structures of Picrasidines L, M, and P," *Chem. Pharm. Bull.* 33(9):3847–3851 (1985).

Ohmoto, T., and Koike, K., "Studies on the alkaloids from *Picrasma quassioides* Bennet. V. Structures of picrasidines L, M, and P," *Chem. Abstr.* 104:65841k (1986).

Ohmoto, T., et al., "Inhibition of Adenosine 3',5'–Cyclic Monophosphate Phosphodiesterase by Alkaloids. II," *Chem. Pharm. Bull.* 36(11):4588–4592 (1988).

Ohmoto, T., et al., "Inhibition of cyclic AMP phosphodiesterase in medicinal plants. Part XV. Inhibition of adenosine 3',5'–cyclic monophosphate phosphodiesterase by alkaloids. II.," *Chem. Abstr.* 110:169068d (1989).

Perel'son, M.E., et al., "Ionization constants of some alkaloids used in medicine," *Khim. Prir. Soedin.* 3:337–341 (1984).

Perel'son, M.E., et al.,"Ionization constants of some alkaloids used in medicine," *Chem. Abstr.* 102:221043t (1985).

Powrie, F., and Coffman, R.L., "Cytokine regulation of T–cell function: potential for therapeutic intervention," *Immunology Today* 14(6):270–274 (1993).

Sadykov, Y.D., and Begovatov, Y.M., "Alkaloids of Cyperus Longus L.," *Izv. Akad. Nauk Tadzh. SSR, Otd. Fiz.–Mat., Khim. Geol. Nauk* 4(118):31–34 (1990).

Sadykov, Y.D., and Begovatov, Y.M., "Alkaloids of Cyperus Longus L.," *Chem. Abstr.* 119:45220p (1993).

Schlecker, W., et al., "Synthesis of 4–Arylpyridines and Substituted β–Carbolines via 1,4–Grignard–Addition to Pyridinecarboxamides," *Tetrahedron* 51(35):9531–9542 (Aug. 1995).

Schlecker, W., et al., "Synthesis of 4–arylpyridines and substituted β–carbolines via 1,4–Grignard–addition to pyridinecarboxamides," *Chem. Abstr.* 124:8655s (Jan. 1996).

Sharipov, I.N., et al., "Homobrevicolline, a new alkaloid of sedge," *Izv. Akad. Nauk Mold. SSR, Ser. Biol. Khim. Nauk* 1:86–88 (1979).

Sharipov, I.N., et al., "Homobrevicolline, a new alkaloid of sedge," *Chem. Abstr.* 91:87295a (1979).

Shirshova, T.I., et al., "Nitration of *Carex parvae* alkaloids," *Khim. Geterotsikl. Soedin.* 7:987–990 (1972).

Shirshova, T.I., et al., "Nitration of *Carex parvae* alkaloids," *Chem. Abstr.* 77:140396y (1972).

Shirshova, T.I., and Terent'eva, I.V., "Reactions in *Carex parva* alkaloids. 6–Aminobrevicolline and 6–bromobrevicolline," *Khim. Geterotsikl. Soedin.* 7:952–953 (1973).

Shirshova, T.I., Terent'eva, I.V., "Reactions in *Carex parva* alkaloids. 6–Aminobrevicolline and 6–bromobrevicolline," *Chem. Abstr.* 79:137341n (1973).

Shirshova, T.I., et al., "Bromination of alkaloids of *Carex parvae*," *Khim. Geterotsikl. Soedin.* 8:1133–1136 (1974).

Shirshova, T.I., et al., "Bromination of alkaloids of *Carex parvae*," *Chem. Abstr.* 81:152482u (1974).

Styngach, E.P., and Semenov, A.A., "Carbolines. III. 1–Methyl–4–tert–butyl–β–carboline," *Khim. Geterotsikl. Soedin.* 5:621–622 (1971).

Styngach, E.P., and Semenov, A.A., "Carbolines. III. 1–Methyl–4–tert–butyl–β–carboline," *Chem. Abstr.* 76:126827n (1972).

Styngach, E.P., et al., "Indole derivatives. VII. Reaction of indole with aziridines," *Khim. Geterotsikl. Soedin.* 8:1066–1069 (1974).

Styngach, E.P., et al., "Indole derivatives. VII. Reaction of indole with aziridines," *Chem. Abstr.* 81:136007n (1974).

Suzuki, H., et al., "Unexpected Debenzylation of N–Benzylindoles with Lithium Base. A New Method of N–Debenzylation," *Tetrahedron Lett.* 36(10):1671–1672 (Mar. 1995).

Suzuki, H., et al., "Synthetic studies on indoles and related compounds. XXXV. Unexpected debenzylation of N–benzylindoles with lithium base. A new method of N–debenzylation," *Chem. Abstr.* 122:290649v (Jun. 1995).

Terent'eva, I.V., et al., "Parvsk sedge by–product alkaloids," *Chem. Abstr.* 74:50497r (1971).

Trudell, M.L., et al., "Hydrazine–Mediated One–Pot Amination–Oxidation Reactions: Facile Synthesis of 4–Amino–β–carbolines and 4–Aminoisoquinolines," *J. Org. Chem.* 52:4293–4296 (1987).

Trudell, M.L., et al., "Hydrazine–mediated one–pot amination–oxidation reaction: facile synthesis of 4–amino–β–carbolines and 4–aminoisoquinolines," *Chem. Abstr.* 107:154264d (1987).

Vember, P.A., et al., "Structure of brevicolline," *Khim. Prir. Soedin.* 4(2):98–101 (1968).

Vember, P.A., et al., "Structure of brevicolline," *Chem. Abstr.* 69:77569z (1968).

Vember, P.A., et al., "The Structure of brevicolline," *Khim. Prir. Soedin.* 3(4):249–253 (1967).

Vember, P.A., et al., "The structure of brevicolline," *Chem. Abstr.* 67:108816t (1967).

Voronin, V.V., et al., "Prophylaxis of postpartum complications in cows," *Veterinariya (Moscow)* 3:57–59 (1979).

Voronin, V.V., et al., "Prophylaxis of postpartum complications in cows," *Chem. Abstr.* 90:197765r (1979).

Waldmann, T.A., "The IL–2/IL–2 receptor system: a target for rational immune intervention," *Immunology Today* 14(6):264–270 (1993).

English–language abstract of German Patent Publication No. DE 3240514, Derwent World Patents Index Accession No. 84–115276.

English–language abstract of Japanese Patent Publication No. 07–112918, Patent Abstracts of Japan.

International Search Report for International Application No. PCT/US97/13767.

Kaempfer, Raymond, Regulation of the Human Interleukin–2/Interleukin–2 Receptor System: A Role for Immunosuppression (43737), P.S.E.B.M. 1994 vol. 206; 176–180.

Baine, Yaela, et al, Functional Characterization of Novel IL–2 Transcriptional Inhibitors, The Journal of Immunology 1995, 154, p. 3667–3677.

4-SUBSTITUTED BETA-CARBOLINES AND ANALOGS THEREOF

RELATED APPLICATIONS

The benefit of U.S. provisional application Serial No. 60/023,650, filed Aug. 9, 1996, is hereby claimed.

TECHNICAL FIELD OF THE INVENTION

This invention relates to 4-substituted β-carbolines and analogs thereof that inhibit $Ca^{+2}$ influx and interleukin-2 (IL-2) production. In one embodiment, this invention relates to a novel class of 4-substituted β-carbolines and β-carboline analogs and pharmaceutical compositions comprising these compounds. This invention also relates to methods for producing β-carbolines. Because of their selective immunomodulating properties, the compounds and pharmaceutical compositions of this invention are particularly well suited for preventing and treating immune disorders, including autoimmune disease, inflammatory disease, organ transplant rejection and other disorders associated with IL-2 mediated immune response.

BACKGROUND OF THE INVENTION

It has been well established that T-cells play an important role in regulating immune response (F. Powrie and R. L. Coffman, *Immunol. Today*, 14, p. 270 (1993)). Indeed, activation of T-cells is often the initiating event in many inflammatory and autoimmune diseases. IL-2 is an autocrine growth factor which plays an essential role in the regulation of T-cell activation and proliferation. Furthermore, influx of extracellular calcium is necessary to achieve the elevated intracellular calcium levels required to initiate IL-2 gene transcription (W. Jy et al., *BBA*, 983, 153 (1989); S. C. Chung et al., *Br. J. Pharmacol.*, 113, 861 (1994)). Inhibition of $Ca^{+2}$ influx would therefore inhibit IL-2 production. Clinical studies have shown that interference with IL-2 activity effectively suppresses immune response in vivo (T. A. Waldmann, *Immunol. Today*, 14, 270 (1993)). Accordingly, agents which inhibit $Ca^{+2}$ influx and IL-2 production are therapeutically useful for selectively suppressing immune response in a patient in need of such immunosuppression.

Previously, others have attempted to interfere with the activity of IL-2 by using cytokine antagonists, monoclonal antibodies, toxins and other biologics which seek to prevent IL-2 from binding to its receptor (G. Mazur and I. Frydecka, *Acta Haematol. Pol.*, 24(4), p. 307 (1993)). More recently, others have attempted to inhibit IL-2 production at the T cell level. However, to date, the reported compounds suffer from several disadvantages such as low potency, poor in vivo activity, cellular toxicity and poor oral bioavailability. Accordingly, a need exists for compounds that can effectively inhibit IL-2 production for preventing and treating immune disorders.

The compounds of this invention are 4-substituted β-carbolines and β-carboline analogs that are either unsubstituted or substituted with halo or $C_1-C_3$ alkyl in the 1- and 3-positions. In general, a limited number of 4-substituted β-carbolines are known in the art (see, for example, U.S. Pat. No. 5,010,077; Kuchova et al., *Chem. Heterocycl. Compd.*, 6, 182 (1970); Haider and Plas, *Tetrahedron*, 46(10), 3641 (1990); Efremova et al., *Chem. Heterocycl. Compd.*, 10, 1210 (1974); Fukada et al., *Tetrahedron Lett.*, 26(18), 2139 (1985) and published PCT International Application No. WO 96/22989). Prior to this invention, however, there was no recognition or appreciation of the efficacy of 4-substituted β-carbolines or β-carboline analogs as inhibitors of $Ca^{+2}$ influx and IL-2 production.

SUMMARY OF THE INVENTION

This invention satisfies the need for potent and selective inhibitors of $Ca^{+2}$ influx and IL-2 production by providing 4-substituted β-carbolines and β-carboline analogs having the desired activity. These 4-substituted β-carboline inhibitors are represented by formula (I):

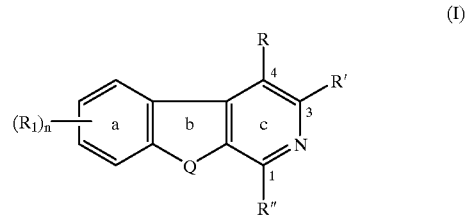

wherein:

Q is selected from the group consisting of N—$R_2$, O or S;

n is an integer selected from the group consisting of 0, 1, 2, 3 and 4;

R is selected from the group consisting of $COR_4$, $CO_2R_4$, $C_3-C_8$ cycloalkyl, $C_1-C_6$ branched or unbranched alkyl, $C_2-C_6$ branched or unbranched alkenyl, $C_2-C_6$ branched or unbranched alkynyl, $C_1-C_6$ branched or unbranched alkoxy, halogen, $NR_3R_4$, phenyl optionally substituted with one or more independently selected $R_1$, benzyl optionally substituted with one or more independently selected $R_1$, naphthyl optionally substituted with one or more independently selected $R_1$ and heterocycles optionally substituted with one or more independently selected $R_1$;

R' and R" are independently selected from the group consisting of H, halo and $C_1-C_3$ alkyl;

each $R_1$, if present, is independently selected from the group consisting of OH, nitro, $NR_3R_4$, $COR_4$, $CO_2R_4$, cyano, halo, $C_3-C_8$ cycloalkyl, $C_3-C_8$ cycloalkenyl, $C_1-C_6$ branched or unbranched alkyl, $C_2-C_6$ branched or unbranched alkenyl, $C_2-C_6$ branched or unbranched alkynyl, $C_1-C_6$ branched or unbranched alkoxy, wherein said cycloalkyl, cycloalkenyl, alkyl, alkenyl, alkynyl or alkoxy may be optionally substituted with one to three substituents (the same or different) independently selected from the group consisting of OH, $NR_3R_4$, $COR_4$, $CO_2R_4$, cyano and halo;

$R_2$ is selected from the group consisting of H, an amino protecting group, $C_1-C_6$ branched or unbranched alkyl, $C_2-C_6$ branched or unbranched alkenyl, $C_2-C_6$ branched or unbranched alkynyl and benzyl;

each $R_3$ is independently selected from the group consisting of H, $C_1-C_6$ branched or unbranched alkyl; $C_2-C_6$ branched or unbranched alkenyl, $C_2-C_6$ branched or unbranched alkynyl, $C_1-C_6$ branched or unbranched alkoxy, phenyl and benzyl; and each $R_4$ is independently selected from the group consisting of H, phenyl and $C_1-C_6$ branched and unbranched alkyl optionally substituted with phenyl.

Another object of this invention is to provide novel 4-substituted β-carbolines and β-carboline analogs of formula (I) wherein the definitions of n, Q, R, R', R" and $R_1-R_4$ are as shown above with the proviso that R excludes pyridinylmethyl, 1-methyl-imidazolyl-2-yl-methyl, unsubstituted phenyl, hydroxymethyl, amino, allyloxyl and trimethylsilanyl.

Yet another object of this invention is to provide pharmaceutical compositions comprising the 4-substituted β-carbolines and β-carboline analogs of this invention and methods for their use in suppressing immune function.

A further object of this invention is to provide convenient methods for producing β-carbolines and β-carboline analogs.

These and other objects will be readily apparent to those of ordinary skill in the art based upon the following detailed disclosure of this invention.

DETAILED DESCRIPTION OF THE INVENTION

In order that the invention herein described may be more fully understood, the following detailed description is set forth. As used herein, the following abbreviations are used:
Bn=Benzyl
BOC or t-BOC=tertiary butoxycarbonyl
chloranil=2,3,5,6-tetrachloro-1,4-benzoquinone
DDQ=2,3-dichloro-5,6-dicyano-1,4-benzoquinone
DMAP=4-dimethylamino pyridine
Et=ethyl
Me=methyl
Ph=phenyl
Pr=propyl
Pyr=pyridine
TFA=trifluoroacetic acid
THF=tetrahydrofuran The following terms are used herein:

The term "heterocycle" refers to a stable 5–7 membered (but preferably, 5 or 6 membered) monocyclic or 8–11 membered bicyclic heterocycle which may be either saturated or unsaturated and which may be optionally benzo-fused if monocyclic. Each heterocycle consists of carbon atoms and from 1 to 4 heteroatoms selected from the groups consisting of nitrogen, oxygen and sulfur. As used herein, "nitrogen" and "sulfur" include any oxidized form of nitrogen and sulfur and the quaternized form of any basic nitrogen. The heterocycle may be attached by any atom of the cycle which results in the creation of a stable structure. Preferred heterocycles include, for example, benzimidazolyl, imidazolyl, imidazolinoyl, imidazolidinyl, quinolyl, isoquinolyl, indolyl, oxadiazolyl, pyridyl, pyrrolyl, pyrrolinyl, pyrazolyl, pyrzinyl, quinoxolyl, piperidinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazolyl, benzodioxolyl, tetrahydrothiophenyl and sulfolanyl. Even more preferred heterocycles of this invention (especially with respect to the definition of R) include imidazolyl, oxadiazolyl, pyridyl, pyrrolyl, pyrazolyl, piperidinyl, morpholinyl, furyl, thienyl, and thiazolyl. Most preferred heterocycles of this invention invention (especially with respect to the definition of R) include: oxadiazolyl, thienyl and furyl.

The term "nitrogen protecting group" in connection with the indole nitrogen in the core β-carboline structure represented in formula (I) refers to any known nitrogen protecting group that results in the formation of a stable structure. Preferred nitrogen protecting groups include acyl, alkoxycarbonyl (such as Boc) and alkyl or aryl sulfonyl protecting groups.

The term "patient" refers to a warm-blooded mammal and preferably, a human.

The term "prevention" or "prophylaxis" refers to a measurable reduction in the likelihood of a patient acquiring a disease or disorder. The term "treatment" refers to either the alleviation of the physical symptoms of a disease or an improvement in the physiological markers used to measure progression of a disease state.

The term "pharmaceutically acceptable carrier" of "pharmaceutically acceptable adjuvant" refers to a non-toxic carrier or adjuvant that may be administered to a patient together with a compound of this invention and which does not destroy the pharmacological activity of that compound.

The term "pharmaceutically effective amount" refers to an amount effective in suppressing the immunity of a patient in need of such treatment. Suppressed immunity can be readily measured by observing the degree of inhibition of IL-2 production in human T-cells (PBLs) by known techniques. The term "prophylactically effective amount" refers to an amount effective in preventing or reducing the likelihood of initial onset or progression of an immune disorder in a patient susceptible to such disorder.

The term "$R_1$" as used in connection with the core β-carboline structure represented in formula (I) may occur from 0–4 times, each occurrence being independently selected and being the same as or different from other occurrences of $R_1$ in the structure. If n is 0, then the a-ring of the core β-carboline structure is unsubstituted. As a substituent on a phenyl, benzyl, naphthyl or heterocyclic moiety (i.e., in connection with the definition of R), the term "$R_1$" may occur, if at all, one or more times and up to the maximum number of possible substitutions in a given phenyl, benzyl, naphthyl or heterocyclic moiety, each occurrence being independently selected and being the same as or different from other occurrences of $R_1$ in the structure. Preferably, when a phenyl or benzyl is substituted with one or more $R_1$, $R_1$ occurs from one to three times (and more preferably, two times and most preferably one time in the para-position). Preferably, when a naphthyl or a heterocycle is substituted with one or more $R_1$, $R_1$ occurs from one to four times (and more preferably, one to three times and most preferably, one time).

It should be understood that any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

The compounds of this invention are defined to include pharmaceutically acceptable derivatives thereof. A "pharmaceutically acceptable derivative" refers to any pharmaceutically acceptable salt, ester, or salt of an ester of a compound of this invention, or any other compound which, upon administration to a patient, is capable of providing (directly or indirectly) a compound of this invention, a pharmacologically active metabolite or pharmacologically active residue thereof.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids.

Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal; (e.g., sodium), alkaline earth metal (e.g., magnesium), ammonium and N-$(C_1-C_4 \text{ alkyl})_4^+$ salts.

Combinations of substituents and variables encompassed by this invention are only those that result in the formation of stable compounds. The term "stable" as used herein, refers to compounds which possess stability sufficient to permit manufacture and administration to a patient by conventional methods known in the art. Typically, such compounds are stable at a temperature of 40° C. or less, in the absence of moisture or other chemically reactive conditions, for at least a week.

The compounds of this invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The compounds of this invention also include those compounds with quaternization of any basic nitrogen-containing groups contained therein. The basic nitrogen can be quaternized with any agents known to those of ordinary skill in the art, including, for example, lower alkyl halides, such as methyl, ethyl, propyl and butyl chlorides, bromides and iodides; dialkyl sulfates including dimethyl, dibutyl and diamyl sulfates; long chain halides such as decyl, lauryl, myristyl and stearyl chlorides, bromides and iodides; and aralkyl halides including benzyl and phenethyl bromides. Water or oil soluble or dispersible products may be obtained by such quaternization.

The 4-substituted β-carbolines and β-carboline analogs of this invention are represented by formula (I):

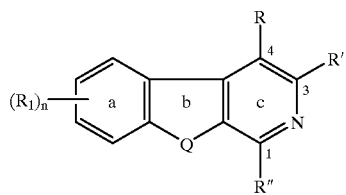

(I)

wherein:
Q is selected from the group consisting of N—$R_2$, O or S;
n is an integer selected from the group consisting of 0, 1, 2, 3 and 4;
R is selected from the group consisting of $COR_4$, $CO_2R_4$, $C_3-C_8$ cycloalkyl, $C_1-C_6$ branched or unbranched alkyl, $C_2-C_6$ branched or unbranched alkenyl, $C_2-C_6$ branched or unbranched alkynyl, $C_1-C_6$ branched or unbranched alkoxy, halogen, $NR_3R_4$, phenyl optionally substituted with one or more independently selected $R_1$, benzyl optionally substituted with one or more independently selected $R_1$, naphthyl optionally substituted with one or more independently selected $R_1$ and heterocycles optionally substituted with one or more independently selected $R_1$;
R' and R" are independently selected from the group consisting of H, halo and $C_1-C_3$ alkyl;
each $R_1$, if present, is independently selected from the group consisting of OH, nitro, $NR_3R_4$, $COR_4$, $CO_2R_4$, cyano, halo, $C_3-C_8$ cycloalkyl, $C_3-C_8$ cycloalkenyl, $C_1-C_6$ branched or unbranched alkyl, $C_2-C_6$ branched or unbranched alkenyl, $C_2-C_6$ branched or unbranched alkynyl, $C_1-C_6$ branched or unbranched alkoxy, wherein said cycloalkyl, cycloalkenyl, alkyl, alkenyl, alkynyl or alkoxy may be optionally substituted with one to three substituents (the same or different) independently selected from the group consisting of OH, $NR_3R_4$, $COR_4$, $CO_2R_4$, cyano and halo;
$R_2$ is selected from the group consisting of H, an amino protecting group, $C_1-C_6$ branched or unbranched alkyl, $C_2-C_6$ branched or unbranched alkenyl, $C_2-C_6$ branched or unbranched alkynyl and benzyl;
each $R_3$ is independently selected from the group consisting of H, $C_1-C_6$ branched or unbranched alkyl; $C_2-C_6$ branched or unbranched alkenyl, $C_2-C_6$ branched or unbranched alkynyl, $C_1-C_6$ branched or unbranched alkoxy, phenyl and benzyl; and
each $R_4$ is independently selected from the group consisting of H, phenyl and $C_1-C_6$ branched and unbranched alkyl optionally substituted with phenyl.

The novel 4-substituted β-carbolines and β-carboline analogs of formula (I) wherein the definitions of n, Q, R, R', R" and $R_1-R_4$ are as shown above, with the proviso that R excludes pyridinylmethyl, 1-methyl-imidazolyl-2-yl-methyl, unsubstituted phenyl, hydroxymethyl, amino, allyloxyl and trimethylsilanyl. Preferably, R' is H when R is $C_1-C_6$ branched or unbranched alkyl, $C_2-C_6$ branched or unbranched alkenyl, $C_2-C_6$ branched or unbranched alkynyl, $C_1-C_6$ branched or unbranched alkoxy, $COR_4$ or $CO_2R_4$. In an alternate and preferred embodiment, the novel 4-substituted β-carbolines and β-carboline analogs of formula (I) are those compounds having the definitions of n, Q, R, R', R" and $R_1-R_4$ as shown above, with the proviso that R excludes pyridinylmethyl, 1-methyl-imidazolyl-2-yl-methyl, unsubstituted phenyl, hydroxymethyl, amino, allyloxyl, trimethylsilanyl, $C_1-C_6$ branched or unbranched alkyl, $C_2-C_6$ branched or unbranched alkenyl, $C_2-C_6$ branched or unbranched alkynyl, $C_1-C_6$ branched or unbranched alkoxy, $COR_4$ and $CO_2R_4$.

Preferably, the novel 4-substituted β-carbolines and β-carboline analogs of formula (I) are those compounds wherein n, Q, R" and $R_1-R_4$ are defined as above, R' is H and R is selected from the group consisting of $C_3-C_9$ cycloalkyl (preferably cyclopentyl or cyclohexyl), 3–8 membered heterocyclyl, benzyl and phenyl, wherein said benzyl and phenyl are substituted with one to three $R_1$ and said heterocyclyl is optionally substituted with one to two $R_1$. More preferably, when R' is H, R is selected from the group consisting of 5–6 membered heterocyclyl, benzyl and phenyl, wherein said heterocyclyl, benzyl and phenyl are substituted with one group (preferably para-substituted in the case of benzyl and phenyl) or two groups independently selected from $C_1-C_3$ alkoxy, $C_1-C_3$ alkyl and $C_1-C_3$ fully or partially halogenated (preferably, fluorinated) alkyl.

More preferably, the novel 4-substituted β-carbolines and β-carboline analogs of this invention are those compounds of formula (I) wherein one or more of the following definitions apply:

Q is N—$R_2$;

n is 0, 1 or 2;

R is selected from the group consisting of $C_3$–$C_8$ cycloalkyl (preferably cyclopentyl or cyclohexyl), 3–8 membered heterocyclyl (preferably, 5–6 membered heterocyclyl), benzyl and phenyl, wherein said heterocyclyl, benzyl and phenyl are substituted with one (in the case of benzyl and phenyl, preferably para-substituted) or two groups independently selected from $C_1$–$C_3$ alkoxy, $C_1$–$C_3$ alkyl and $C_1$–$C_3$ fully or partially halogenated (preferably, fluorinated) alkyl;

R' is H;

R" is selected from H and methyl;

$R_1$, if present, is selected from the group consisting of OH, amino, halo (preferably, F, Br or Cl), $C_1$–$C_3$ alkoxy, $C_1$–$C_3$ alkyl (preferably, ethyl or methyl) optionally substituted with OH, and $C_1$–$C_3$ halogenated alkyl (preferably, trifluoromethyl) optionally substituted with OH; and $R_2$ is selected from the group consisting of H, $C_1$–$C_3$ alkyl optionally substituted with phenyl.

Even more preferably, the compounds of formula (I) are those wherein one or more of the following definitions apply:

Q is N—$R_2$;

n is 0 or 1;

R is selected from the group consisting of oxadiazolyl, thienyl, furyl, thiazolyl (wherein said oxadiazolyl, thienyl, furyl and thiazolyl are optionally substituted with one or two groups independently selected from $C_1$–$C_3$ alkoxy, $C_1$–$C_3$ alkyl and $C_1$–$C_3$ fully or partially halogenated (preferably, fluorinated) alkyl) and phenyl substituted with one (preferably para-substituted) or two groups independently selected from $C_1$–$C_3$ alkoxy, $C_1$–$C_3$ alkyl and $C_1$–$C_3$ fully or partially halogenated (preferably, fluorinated) alkyl;

R' and R" are both H;

$R_1$, if present, is selected from the group consisting of halo, $C_1$–$C_3$ alkyl and $C_1$–$C_3$ alkoxy; and $R_2$ is selected from the group consisting of H, $C_1$–$C_3$ alkyl optionally substituted with phenyl.

Compounds of formula (I) wherein R is an optionally substituted phenyl may be generally prepared by the reaction sequence shown in Scheme 1:

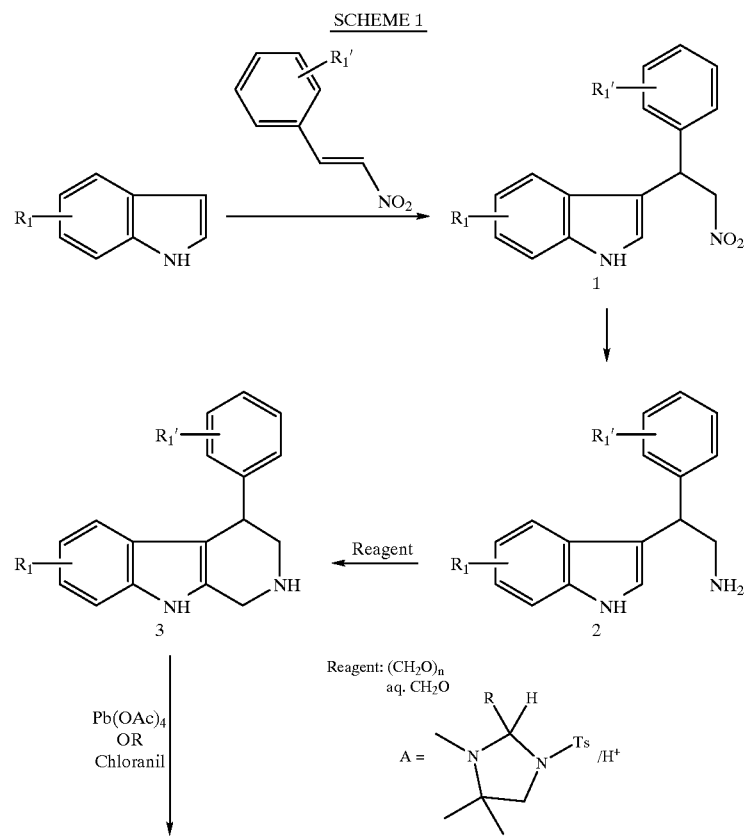

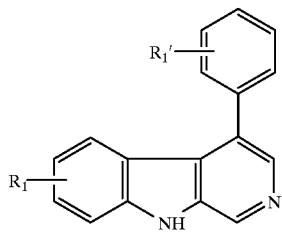

Scheme 1 sets forth a method for preparing a compound of formula (I) comprising the steps of:

(a) reacting a substituted indole with trans β-nitrostyrene or trans o-substituted, m-substituted or p-substituted-β-nitrostyrene to give a substituted 3-(2-nitro)ethyl indole;

(b) reducing the substituted 3-(2-nitro)ethyl indole in the presence of a catalyst to produce an 3-(2-amino)ethyl indole;

(c) treating the 3-(2-amino)ethyl indole with 1-tosyl-3,4,4-trimethylimidazolidine to produce a tetrahydro-β-carboline derivative; and (d) aromatizing the tetrahydro-β-carboline derivative to produce the compound of formula (I).

More specifically, according to Scheme 1, an appropriately substituted indole is reacted with trans β-nitrostyrene or trans o-substituted, m-substituted or p-substituted-β-nitrostyrene through a Michael addition to give compound 1. This reaction can be run in an inert solvent, such as toluene, xylene or n-butanol, or without solvent, at an appropriate temperature (typically ranging between 90°–100° C.). If the appropriately substituted β-nitrostyrene is not available commercially, it may be readily prepared by condensing an appropriately substituted benzaldehyde with nitromethane. Compound 1 is readily reduced in the presence of a catalyst such as Raney-Nickel or Pd/C to give the indole ethylamine derivative 2. The formation of the tetrahydro-β-carboline ring system is carried out by the treatment with paraformaldehyde/H+ or aqueous formaldehyde or with 1-tosyl-3,4,4-trimethylimidazolidine A. The use of reagent A provides the best result. The preferred solvents for this reaction are acetonitrile and 10% HOAc (Hiemestra et al., Tetrahedron, 39 (23), 3981 (1983)).

An alternate route to the compounds of formula (I) is illustrated in Scheme 2:

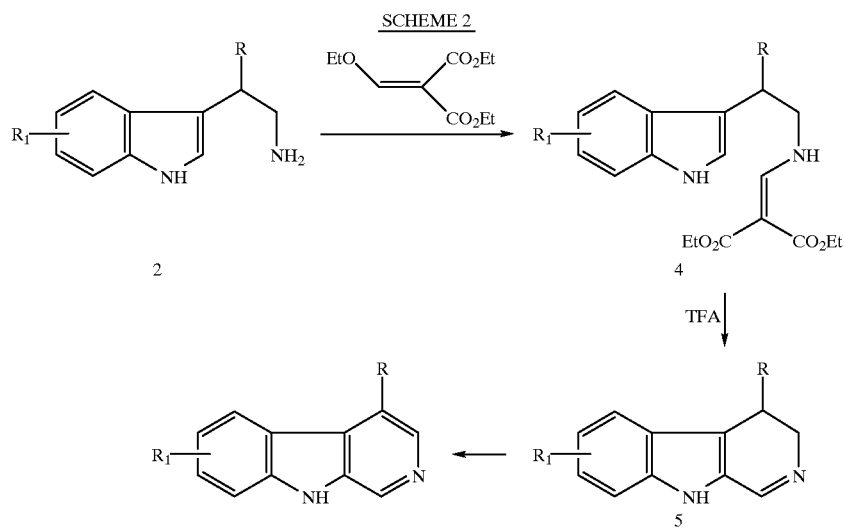

Scheme 2 sets forth a method for producing a compound of formula (I) comprising the steps of:

(a) reacting a 3-(2-amino)ethyl indole derivative with diethyl ethoxymethylenemalonate to produce a coupled malonate derivative;

(b) treating the coupled malonate derivative with TFA to produce a 3,4-dihydro-β-carboline derivative; and (c) aromatizing the 3,4-dihydro-β-carboline derivative to produce the compound of formula (I).

More specifically, according to Scheme 2, the 3-(2-amino) ethyl indole derivative 2 undergoes reaction with diethyl ethoxymethylenemalonate in a polar solvent (such as EtOH) to give 4. Upon treatment of 4 with TFA, internal ring closure results in the formation of intermediate 5. The final compound may be obtained by oxidation of 5 using oxidizing agents such as chloranil or DDQ.

A further alternative reaction scheme is shown in Scheme 3:

SCHEME 3

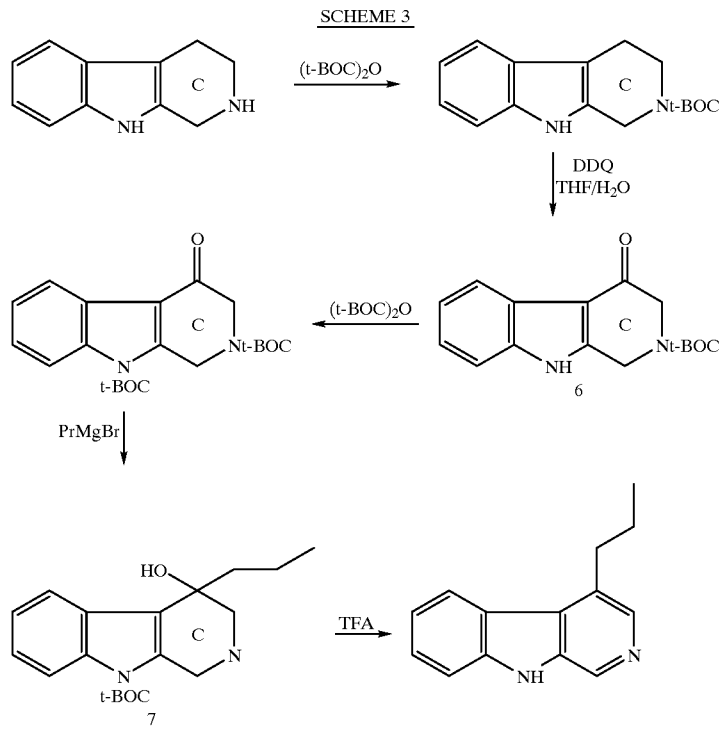

Scheme 3 sets forth a method for producing a compound of formula (I) comprising the steps of:

(a) oxidizing a substituted tetrahydro-β-carboline in which the c-ring is N-protected to produce a 4-oxo derivative;

(b) protecting the indole nitrogen with a nitrogen protecting group to produce an N,N-di-protected 4-oxo derivative;

(c) treating the N,N-di-protected 4-oxo derivative with a Grignard reagent to produce a 4-substituted, 4-hydroxy N,N-di-protected derivative; and (d) reacting the 4-substituted, 4-hydroxy N,N-di-protected derivative with TFA to produce a compound of formula (I).

More specifically, the synthesis shown in Scheme 3 starts with a substituted tetrahydro-β-carboline and protects the C-ring nitrogen using a protecting group, such as tertiary-butoxycarbonyl (t-BOC). The N-protected tetrahydro-β-carboline is then oxidized with DDQ to give the 4-oxo derivative 6. Protection of the indole nitrogen (e.g., with t-BOC), followed by treatment with a Grignard reagent gives 7. 7 is converted to the final product in one step using trifluoroacetic acid (TFA). In this conversion, deprotection, dehydration and oxidation occur in a single step.

As can be appreciated by chemists possessing ordinary skill in the art, the synthetic schemes described above are for illustrative purposes only and may be modified using conventional synthetic methodology to produce any of the β-carbolines or β-carboline analogs of formula (I). Depending on precisely how the synthetic schemes are modified, the specific reaction conditions might also require modification. Such modifications may involve the use of higher or lower temperature or pressure conditions than those reported herein or the addition of further synthetic steps, such as functional group transformations. However, since progress of the reactions is easily monitored by techniques such as high performance liquid chromatography, gas chromatography, mass spectroscopy, thin layer chromatography, nuclear magnetic resonance spectroscopy and the like, such modifications are well within the skill of the art.

The 4-substituted β-carbolines and β-carboline analogs of formula (I) inhibit production of IL-2. Without wishing to be bound by theory, the compounds of this invention inhibit IL-2 production by T cells by inhibiting extracellular calcium influx. This inhibition of IL-2 production is therapeutically useful for selectively suppressing immune function. The result of such selectively suppressed immunity includes reduced immunoglobulin synthesis, cell proliferation of peripheral blood lymphocytes and cellular immune response without serious toxicity or undesired side effects. Thus, the inhibition of IL-2 production is an attractive means for preventing and treating a variety of immune disorders, including inflammatory diseases, autoimmune diseases, organ and bone marrow transplant rejection and other disorders associated with IL-2 mediated immune response. In particular, the compounds of formula (I) may be used to prevent or treat acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease (and other forms of organ or bone marrow transplant rejection) and lupus erythematosus. Other disorders associated with IL-2 mediated immune response will be evident to those of ordinary skill in the art and can also be treated with the compounds and compositions of this invention.

The compounds of this invention may be administered in any conventional dosage form in any conventional manner. Such methods of treatment, including their dosage levels and other requirements, may be selected by those of ordinary skill in the art from available methods and techniques. For example, a compound of this invention may be combined with a pharmaceutically acceptable carrier or adjuvant for administration to a patient in need of such treatment in a pharmaceutically acceptable manner and in an amount effective to treat (including lessening the severity of symptoms) the immune disorder.

The compounds of this invention may be administered alone or in combination with conventional therapeutics, such as conventional immunosuppressants. Advantageously, such combination therapies utilize lower dosages of the conventional therapeutics, thus avoiding possible toxicity and adverse side effects incurred when those agents are used as monotherapies. The compounds of this invention may be physically combined with the conventional therapeutics into a single pharmaceutical composition. Advantageously, the compounds may then be administered together in a single dosage form. Preferably, the pharmaceutical compositions comprising such combinations of compounds contain at least about 15%, but more preferably at least about 20%, of a compound of formula (I) (w/w). Alternatively, the compounds may be administered separately (either serially or in parallel). Separate dosing allows for greater flexibility in the dosing regime.

According to this invention, the compounds of formula (I) and the pharmaceutical compositions containing those compounds may be administered to a patient in any conventional manner and in any pharmaceutically acceptable dosage from, including, but not limited to, intravenously, intramuscularly, subcutaneously, intrasynovially, by infusion, sublingually, transdermally, orally, topically or by inhalation. The preferred modes of administration are oral and intravenous.

Dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, Pharmaceutical Dosage Forms and Drug Delivery Systems, 5th ed., Lea and Febiger (1990)). Dosage levels and requirements are well-recognized in the art and may be selected by those of ordinary skill in the art from available methods and techniques suitable for a particular patient. Typically, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto and the judgment of the treating physician.

In order that this invention be more fully understood, the following examples are set forth. These examples are for the purpose of illustrating preferred embodiments of this invention, and are not to be construed as limiting the scope of the invention in any way.

EXAMPLE 1

Synthesis of 4-(p-Methylphenyl)-β-carboline (Compound 1)

A. Trans-p-methyl-β-nitrostyrene

A mixture of 12.0 g (0.1 mol) of 4-methylbenzyl aldehyde, 5.4 g (0.09 mol) of nitromethane and 1.0 mL of aniline was stirred at 110° C. overnight. The reaction mixture was diluted with hexane and the yellow crystalline product was filtered, the filtered cake was washed well with hexane. This was recrystallized from $CH_2Cl_2$/hexane to give 3.26 g of product (20% yield) with m.p. 101°–102° C. This was used in the following step.

B. 3-[1-(p-methylphenyl)-2-nitro]ethylindole

A mixture of 3.26 g (20 mmol) of trans p-methyl-β-nitrostyrene and 3.66 g (20 mmol) of indole was heated at 100° C. for 24 h. The resulting mixture, after cooling, was purified on silica gel column using $CH_2Cl_2$ as the eluant to give 4.6 g (82%) of final product in the form of a reddish resin.

C. 3-[1-(p-methylphenyl)-2-amino]ethylindole

To a solution of 3.62 g (12.9 mmol) of 3-[1-(p-methylphenyl)-2-nitro]ethylindole in 150 mL of absolute EtOH was added excess Raney-Nickel as 50% slurry in water with pH>9. The resulting mixture was hydrogenated on a Parr shaker overnight. The catalyst Raney-Nickel was filtered off with the aid of Celite and the filtrate was concentrated to give a residue which was crystallized from $CH_2Cl_2$/hexane to give 2.85 g (88.6% yield) of solid, m.p. 107°–108° C.

D. 4-(p-Methylphenyl)tetrahydro-β-carboline

A mixture of 250 mg (1 mmol) of 3-[1-(p-methylphenyl)-2-aminoindole and 267 mg (1 mmol) of 1-tosyl-3,4,4-trimethylimidazolidine in 1 mL of acetic acid and 5 mL of acetonitrile was kept under reflux for 2 h. The reaction mixture was concentrated and the residue was dissolved into $CH_2Cl_2$. The $CH_2Cl_2$ solution was washed with saturated $NaHCO_3$, dried over anhydrous $Na_2SO_4$, filtered and concentrated. Flash column chromatography starting with 1:1 EtOAc/hexane and followed by 10% MeOH in $CH_2Cl_2$. Most of the product were collected from the 10% MeOH/$CH_2Cl_2$ fractions. After crystallization from $CH_2Cl_2$/hexane, a crystalline product weighed 209.2 mg (80% yield) was obtained, m.p. 223°–224° C. Elemental Analysis Calcd for $C_{18}H_{18}N_2 \cdot 1/4H_2O$: C, 81.00; H, 6.98; N, 10.53. Found: C, 81.07; H, 6.93; N, 10.53.

E. 4-(p-Methylphenyl)-β-carboline

To a solution of 500 mg (1.91 mmol) of 4-(p-methylphenyl)tetrahydro-β-carboline in 7.6 mL of acetic acid was added 1.65 g (3.72 mmol) of $Pb(OAc)_4$ with cooling. After stirring for 25 min., 1.85 g (20.5 mmol) of oxalic acid was added. The resulting mixture was stirred for an additional 60 min. with cooling. The pale yellow precipitate was filtered and washed with MeOH. The yellow precipitate was suspended in 16 mL of $H_2O$ and 32 mL of $CH_2Cl_2$ and the suspension was neutralized with saturated $NaHCO_3$. The aqueous phase was extracted with $CH_2Cl_2$ several times and the combined $CH_2Cl_2$ extracts were washed with brine, dried and concentrated to give a crude product weighed 440 mg (89.2% yield). After several crystallization from $CH_2Cl_2$/hexane/MeOH, 98.5 mg of the pure product was obtained (20% yield), m.p. 225°–226° C. Elemental Analysis Calcd for C18 H14 N2: C, 83.69; H, 5.46; N, 10.84. Found: C, 83.44; H, 5.52; N, 10.77.

EXAMPLE 2

Synthesis of 4-Phenyl-β-carboline (Compound 2)

A. 4-Phenyl-3,4-dihydro-β-carboline

The preparation of 3-(1-phenyl-2-nitro)ethylindole was achieved as described in Example 1. A mixture of 1.36 g (5.76 mmol) of 3-(1-phenyl-2-nitro)ethylindole and 1.246 g (5.76 mmol) of diethyl ethoxymethylenemalonate in 75 mL toluene was refluxed overnight. Sovent, toluene was removed on rotary evaporator and the residue was passed through a short column to give 1.9 g using 1:1 pet-ether/ CH$_2$Cl$_2$. This matrial was crytallized from CH$_2$Cl$_2$/pet-ether to give 1.4 g (50%) pure derivative of 4. A 1.2 g (2.7 mmol) of 4 was treated with 10 mL TFA. After 2 h. at r.t., the reaction mixture was concentrated and the residue was treated with saturated Na$_2$CO$_3$ to pH 7. The aqueous phase was extracted with CH$_2$Cl$_2$. The combined CH$_2$Cl$_2$ extracts were washed with brine, dried and concentrated to give 710 mg of crude product. The crude material was crystallized from CH$_2$Cl$_2$ to afford 450 mg of product, m.p. 186°–187° C. Elemental Analysis Calcd for C17 H14 N2: C, 82.90; H, 5.73; N, 11.37. Found: C, 82.69; H, 5.90; N, 10.97.

B. 4-Phenyl-β-carboline

To a solution of 180 mg (0.73 mmol) of 4-phenyl-3,4-dihyro-β-carboline in 20 mL of dioxane, heating was necessary to bring the compound into solution, and 202 mg (1.47 mmol) of K$_2$CO$_3$ was added 331.8 mg (1.47 mmol) of DDQ. The reaction was stirred at r.t. for 0.5 h. when TLC indicated that the reaction was completed. The reaction was diluted with H$_2$O and extracted with ether (3×). The combined ether extracts were washed with brine, dried and concentrated to give a crude mixture weighed 200 mg. Preparative TLC in 5% MeOH/CH$_2$Cl$_2$ provided 40 mg product. A further recrystallization from CH$_2$Cl$_2$/ether gave 25 mg pure 4-phenyl-β-carboline. MS (NH$_4$Cl): MH$^+$=245 for MW=244; NMR spectrum agreed with the desired product.

EXAMPLE 3

Synthesis of 4-Propyl-β-carboline (Compound 3)

A. N,N-di-t-BOC-4-oxo-tetrahydro-β-carboline

2(N-t-BOC)-4-oxo-tetrahydro-β-carboline was obtained from 2(N-t-BOC)-tetrahydro-β-carboline by the use of DDQ as the oxidizing agent in THF (T. J. Hagen et al., *J. Org. Chem.*, 54, p. 2170 (1989)). To a suspension of 1.01 g (3.53 mmol) of 2(N-t-BOC)-4-oxo-tetrahydro-β-carboline in 75 mL of CH$_2$Cl$_2$ was added 43 mg (0.35 mmol) of DMAP followed by 924 mg (4.24 mmol) of di-t-butyl dicarbonate. The suspension turned into a solution upon additon of di-t-butyl dicarbonate. After 20 minutes at r.t., the reaction was quenched with H$_2$O and extracted with CH$_2$Cl$_2$ (2×). The combined CH$_2$Cl$_2$ extracts were washed with brine, dried and concentrated to give 1.3 g crude product. Flash column chromatography on silica gel starting with pet-ether, 25% CH$_2$Cl$_2$/pet-ether, 50% CH$_2$Cl$_2$/pet-ether to 75% CH$_2$Cl$_2$/pet-ether afforded 1.1 g desired product, most of the product was collected in the 50% CH$_2$Cl$_2$/pet-ether fraction. A 810 mg (59%) white crystalline product was obtained after crystallizing from CH$_2$Cl$_2$/ether.

B. N,N-di-t-BOC-4-hydroxy-4-propyl-tetrahydro-β-carboline

To a solution of 390 mg (1 mmol) of N,N-di-t-BOC-4-oxo-tetrahydro-β-carboline in 20 mL THF was added 1.5 mL (3 mmol) of a 2M PrMgCl in ether. After 1 h. at r.t, the reaction was quenched with H$_2$O and extracted with CH$_2$Cl$_2$ (3×). The combined CH$_2$Cl$_2$ extracts were washed with brine, dried and concentrated to give 410 mg crude product. Preparative TLC in 20% acetone/hexane provided 300 mg (70%) desired product.

C. 4-Propyl-β-carboline

A solution of 340 mg (0.79 mmol) of N,N-di-t-BOC-4-hydroxy-4propyl-tetrahydro-β-carboline in 5 mL TFA was stirred at r.t. for 3 h.. With cooling, the reaction mixture was quenched with saturated Na$_2$CO$_3$ to pH 8. The aqueous phase was extracted several times with CH$_2$Cl$_2$. The combined CH$_2$Cl$_2$ extracts were washed with brine, dried and concentrated to give a crude product weighed 180 mg. Preparative TLC in 10% MeOH/CH$_2$Cl$_2$ afforded 100 mg of a solid which was recrystallized from CH$_2$Cl$_2$/pet-ether to give 73.5 mg (42%) product, m.p. 182°–183° C. Elemental Analysis Calcd for C14 H14 N2. 1/8H$_2$O: C, 79.12; H, 6.75; N. 13.18. Found: C, 79.20; H, 6.60; N, 12.96.

EXAMPLE 4

Synthesis of 4-(p-Trifluoromethylphenyl)-β-carboline (Compound 4)

A. 3-[1-(p-trifluoromethylphenyl)-2-nitro]ethylindole

A mixture of 5 g (23 mmol) of trans p-trifluoromethyl-β-nitrostyrene and 2.7 g (23 mmol) of indole was heated at 80° C. for 2 h. The resulting mixture, after cooling, was purified on silica gel column using CH$_2$Cl$_2$ as the eluant to give 7.49 g (97.5%) of final product in the form of a reddish resin which was used immediately in the next step.

B. 3-[1-(p-trifluoromethylphenyl)-2-amino]ethylindole

To a solution of 7.49 g (22.4 mmol) of 3-[1-(p-trifluoromethylphenyl)-2-nitro]ethylindole in 200 mL of absolute EtOH was added excess Raney-Nickel as 50% slurry in water with pH>9. The resulting mixture was hydrogenated on a Parr shaker overnight. The catalyst Raney-Nickel was filtered off with the aid of Celite and the filtrate was concentrated to give a residue weighed 7.01 g which was crystallized from CH$_2$Cl$_2$/hexane to give 3.35 g (49.2% yield) of solid, m.p. 136°–139° C.

C. 4-(p-Trifluoromethylphenyl)tetrahydro-β-carboline

A mixture of 1.56 g (5.13 mmol) of 3-[1-(p-trifluoromethylphenyl)-2-aminoindole and 1.37 g (mmol) of 1-tosyl-3,4,4-trimethylimidazolidine in 5 mL of acetic acid and 25 mL of acetonitrile was kept under reflux for 2.5 h. The reaction mixture was concentrated and the residue was dissolved into CH$_2$Cl$_2$. The CH$_2$Cl$_2$ solution was washed with saturated NaHCO$_3$, dried over anhydrous Na$_2$SO$_4$, filtered and concentrated. Flash column chromatography starting with 1:1 EtOAc/hexane and followed by 10% MeOH in CH$_2$Cl$_2$. Most of the product was collected from the 10% MeOH/CH$_2$Cl$_2$ fractions. After crystallization from CH$_2$Cl$_2$/hexane, a crystalline product weighing 1.51 g (93% yield) was obtained, m.p. 172°–174° C.

D. 4-(p-Trifluoromethylphenyl)-β-carboline

To a solution of 1.51 g (4.78 mmol) of 4-(p-trifluoromethylphenyl)tetrahydro-β-carboline in 19 mL of acetic acid was added 4.1 g (9.25 mmol) of Pb(OAc)$_4$ with cooling. After stirring for 25 min., 4.7 g (52.2 mmol) of oxalic acid was added. The resulting mixture was stirred for an additional 60 min. with cooling. The pale yellow precipitate was filtered and washed with MeOH. The yellow precipitate was suspended in H$_2$O and CH$_2$Cl$_2$ and the suspension was neutralized with saturated NaHCO$_3$. The aqueous phase was extracted with CH$_2$Cl$_2$ several times and the combined CH$_2$Cl$_2$ extracts were washed with brine, dried and concentrated to give a crude product. After several crystallizations from CH$_2$Cl$_2$/hexane/MeOH, 125 mg of the pure product was obtained (8.4% yield)*, m.p. 274°–275° C. Elemental Analysis Calcd for C18 H11 N2 F3: C, 69.22; H, 3.55; N, 8.96. Found: C, 68.75; H, 3.33; N, 8.84.

*Further extraction of the aqueous phase would increase the yield. Use of a continuous-extractor is recommended for this step.

EXAMPLE 5

Synthesis of 4-(p-Methoxyphenyl)-β-carboline (Compound 5)

A. 3-[1-(p-Methoxyphenyl)-2-nitro]ethylindole

A solid mixture of 8.41 g (71.83 mmol) of indole and 11.7 g (65.3 mmol) of trans p-methoxy-β-nitrostyrene was heated at 110° C. for 6 h. After cooling, a solid precipitate was obtained. The solid was tritrated with $CH_2Cl_2$ (~50 mL) and filtered to give a pure product weighing 10.5 g (54% yield), m.p 148°–149° C.

B. 3-[1-(p-Methoxyphenyl)-2-amino]ethylindole

To a solution of 4 g (13.50 mmol) of 3-[1-(p-methoxyphenyl)-2-nitro]ethylindole in 100 mL of absolute EtOH was added excess Raney-Nickel as 50% sluury in water with pH>9. The resulting mixture was hydrogenated on a Parr shaker for 2 h. The catalyst Raney-Nickel was filtered off with the aid of Celite and the filtrate was concentrated to give an oily residue. The residue was dissolved into $CH_3CN$ to give a solution which on standing afforded a crystalline product weighing 3.3 g (92% yield), m.p. 210°–213° C. (decomposed).

C. 4-(p-Methoxyphenyl)tetrahydro-β-carboline

To a suspension of 3.5 g (13 mmol) of 3-[1-(p-methoxyphenyl)-2-amino]ethylindole in 160 mL of $CH_3CN$ and 13 mL AcOH at 60° C. was added 3.53 g (13.15 mmol) of 1-tosyl-3,4,4-trimethylimidazolidine. A solution was obtained after the addition and some product started to precipitate out as the reaction continuing. The reaction was refluxed for an additional 2 h. After cooling, a first crop of product (1.8 g) was collected as the free base. The filtrate was concentrated to dryness. To this residue was added $CH_2Cl_2$ from which a second crop weighed 1.5 g was collected as a salt with 2 equivalents of AcOH based on $^1$H-NMR. A total yield of 80% was obtained based on the free base.

D. 4-(p-Methoxyphenyl)-β-carboline

To a solution of 1.43 g (3.58 mmol) of 4-(p-methoxyphenyl)tetrahydro-β-carboline in 50 mL glacial AcOH was added 3.18 g (7.16 mmol) of $Pb(OAc)_4$ with stirring at rt. After stiriing at rt for 40 min., 3.22 g (35.8 mmol) of oxalic acid was added. The resulting mixture was kept at rt for 1 h when yellow precipitate appeared. The yellow solid was filtered and the filtered cake was washed with MeOH. The solid product was suspended in 200 mL of $H_2O$ and 200 mL of $CH_2Cl_2$. The pH of the aqueous phase was adjusted to 7 by the addition of solid $NaHCO_3$. The phases were separated and the aqueous phase was extracted 10x, 40 mL each, with $CH_2Cl_2$. The combined $CH_2Cl_2$ extracts were washed with 5% aqueous $NaHCO_3$, dried ($MgSO_4$) and concentrated to ~30 mL to precipitate out 0.62 g of product (63% yield), m.p. 235° C. (decomposed). Elemental Analysis Calcd for $C_{18}H_{14}N_2O$: C,78.81; H,5.14; N,10.21. Found: C,78.68; H,5.27; N, 9.98.

EXAMPLE 6

Other Syntheses

Using procedures analogous to those described above, the following compounds of this inveniton were prepared:

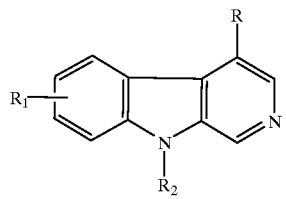

| Compound No. | R | $R_1$ | $R_2$ |
|---|---|---|---|
| 6 | p-OMe-Ph | 6-Cl | H |
| 7 | m-OMe-Ph | H | H |
| 8 | p-OMe-Ph | H | Me |
| 9 | m-Me-Ph | H | H |
| 10 | p-OMe-Ph | H | Bn |
| 11 | o-OMe-Ph | H | H |
| 12 | p-OEt-Ph | H | H |
| 13 | p-Cl-Ph | H | H |
| 14 | 3-Pyr | H | H |
| 15 | p-Me-Ph | 5-Me | H |
| 16 | p-Me-Ph | 6-Me | H |
| 17 | p-Me-Ph | 7-Me | H |
| 18 | p-Me-Ph | 8-Me | H |
| 19 | p-$CO_2$Et-Ph | H | H |
| 20 | p-iPr-Ph | H | H |
| 21 | p-OH-Ph | H | H |
| 22 | p-Me-Ph | 7-OMe | H |
| 23 | p-$CH_2$OH-Ph | H | H |
| 24 | p-$NMe_2$-Ph | H | H |
| 25 | p-benzoyl-Ph | H | H |
| 26 | p-$CF_3$-Ph | H | Me |
| 27 | 2,4-diOMe-Ph | H | H |
| 28 | 3,5-diOMe-Ph | H | H |
| 29 | 3,4-diOMe-Ph | H | H |
| 30 | 2,4-diMe-Ph | H | H |
| 31 | 3,4,5-triOMe-Ph | H | H |
| 32 | 3,4-diCl-Ph | H | H |
| 33 | 3-Me, 4-OMe-Ph | H | H |
| 34 | p-Me-Ph | 7-$CH_2$OH | H |
| 35 | p-Me-Ph | 7-$CO_2$Me | H |
| 36 | p-Me-Ph | 8-$CO_2$Me | H |
| 37 | —$CH_2$—Ph | H | H |
| 38 | cyclohexyl | H | H |
| 39 | 5-Me-2-thienyl | H | H |
| 40 | 4-Me-2-pyridyl | H | H |
| 41 | 5-Me-2-thiazolyl | H | H |
| 42 | 2-naphthyl | H | H |
| 43 | 3-Me-1,2,4-oxadiazol-5-yl | H | H |
| 44 | 3-iPr-1,2,4-oxadiazol-5-yl | H | H |

EXAMPLE 7

Allogeneic Cell Transplant Response in Mice

The ability of cells to recognize other cells from self or from another genetically different individual (non-self) is an important property in maintaining the integrity of tissue and organ structure. The allogeneic cell transplant response is therefore an important model for studies of transplant rejection. This T-cell-mediated immune response can be induced in adult mice by the injection of lymphocytes from an histoincompatible mouse strain. This response is characterized by T cell proliferation which is limited to the popliteal lymph node that receives drainage from the footpad area. No in vitro system exists that can exactly duplicate completely this in vivo response. The assay is commonly used to evaluate new and novel potential immunosuppressive molecules. The assay is preferred to the local GVH response in mice because the magnitude of the response is significantly greater (Kroczek et al., *J. Immunology*, 139, 3597 (1987)).

Experiments are conducted using male or female mice (20–26 grams). Any histoincompatible mouse strains suffice for donor and recipient populations. Typically DBA mice are used as donors and C57B1/6 mice are used as recipients. A minimum of 1 week stabilization and conditioning period is usually required before use of the mice. Each study utilizes approximately 36 recipient mice divided into groups of 6. Previous studies suggest this is the minimum number of animals which yields statistically significant results.

Donor mice are sacrificed by $CO_2$ asphyxiation and spleens are removed and a cell suspension is prepared. The cell suspension ($1.0 \times 10^7$/metatarsal in 0.05 ml) is injected I.D. into the dorsal metatarsal skin of recipient mice. Four days later, the animals are sacrificed by $CO_2$ asphyxiation and the popliteal nodes are removed and weighed. Groups of mice receiving putative immunosuppressive agents are dosed subcutaneously, intraperitoneally or orally one hour prior to cell injection and daily thereafter. The tests last approximately four days. The assay involves no footpad swelling and only a moderate increase in the size of the popliteal lymph node. Student's t test is used to determine significant differences between popliteal lymph nodes of groups of untreated mice and those mice treated with putative immunosuppressive agents.

EXAMPLE 8

IL-2 Promoter Assay

The IL-2 promoter assay measures transcriptional activation of a luciferase reporter gene which has been placed under control of the IL-2 promoter/enhancer. All the known regulatory features of IL-2 gene are contained within a ~300 bp sequence immediately upstream of the open reading frame. The region −328 to +35 relative to the transcription start site of the IL-2 gene is obtained by RT-PCR of human genomic DNA and is subcloned into the promoterless luciferase reporter vector pGL2-Basic (Promega). The resulting construct, pIL2P-luc, and a vector containing a neomycin resistance gene, pcDNA/Neo (Invitrogen), are linearized and stably transfected into Jurkat cells (a human T cell line) by electroporation. Following G-418 selection and dilution cloning, a cell line was established, J.1F/C6., which exhibited a strong induction of luciferase activity upon treatment with ionomycin and PMA (up to 100-fold), and potent inhibition by FK506 ($IC_{50}$=0.3 nM).

For screening compounds, the cells are pelleted by centrifugation, washed once with PBS, resuspended in RPMI (phenol red-free) containing 5% FBS, and dispensed into 96-well, white microtiter plates (Packard) at 50,000 cells/well. The cells are pre-incubated with compounds (1 µg/ml) for 15 min prior to addition of ionomycin (1 µg/ml) and PMA (10 ng/ml) in a final volume of 100 µl. Following a 5 hr incubation at 37° C. in a humidified incubator, 100 µl of Luc-Lite lysis buffer/luciferase assay buffer (Promega) is added and luminescence measured using a Packard Top-Count scintillation counter/luminometer.

EXAMPLE 9

IL-2 Production Assays

Protocol A (ionomycin and PMN as stimuli)

Human peripheral blood is obtained from healthy donors by venipuncture and the mononuclear cell fraction is prepared by centrifugation on Ficoll Hypaque (Phamacia) density gradients. Contaminating red blood cells are lysed and the CD3+/CD4+ cells are purified using immunoaffinity columns (R&D Systems or CellPro). The cells are resuspended and dispensed in 96 well microtiter plates. Test compounds are added to the cells approximately 15 minutes prior to stimulation with ionomycin (1 µg/ml) and PMA (10 ng/ml). The final volume of the assay is 100 µL. Following a 16 hr incubation at 37° C., the cells are pelleted by centrifugation, and the supernatants are collected and stored at −70° C. until assayed for IL-2 using a commercial ELISA kit (Genzyme).

Protocol B (antiCD3/antiCD28 as stimuli)

Human peripheral blood is obtained from healthy donors by venipuncture and the mononuclear cell fraction is prepared by centrifugation on Ficoll Hypaque (Phamacia) density gradients. Contaminating red blood cells are lysed and the CD3+/CD4+ cells are purified using immunoaffinity columns (R&D Systems or CellPro). The T lymphocytes are plated at $1-1.5 \times 10^5$ cells/well in a 96 well microtiter plate, and incubated with serial dilutions of compounds for 20 minutes at 37° C. The T cells are activated by the addition of 0.6 ng/ml anti-CD3 (Immunotech), 500 ng/ml anti-CD28 (Biodesign) and $2 \times 10^5$ goat anti-mouse coated beads (Dynal). The final volume of the assay is 200 µl. Following a 16 hour incubation at 37° C., the cells are pelleted, and the supernatants are removed and collected and stored at −70° C. until assayed for interleukin-2 using a commercial ELISA kit (R&D Systems).

EXAMPLE 10

Calcium Influx Assay

Jurkat cells (clone E6-1) are pelleted by centrifugation, washed twice, and resuspended in RPMI 1640 containing, 10% HEPES, 1 % fetal calf serum, 3 µM Fluo-3-AM, 13.5 µl/ml Pluronic F 127 (Molecular Probes) and incubated for 1 hour at 37° C. The loaded cells are washed twice in Hanks Balanced Salt Solution containing 10 mM HEPES. The cells are resuspended in HBSS containing 10 mM HEPES, and dispensed into 96-well Dynatech black microtiter plates at $2 \times 10^5$ cells/well. The cells are preincubated with compounds for 10 minutes at room temperature. Baseline fluorescence of unstimulated cells is measured using an SLT fluorescent microtiter plate reader with an excitation wavelength of 495 nm and emission wavelength of 538 nm. Thapsigargin is then added to a final concentration of 100 nM. Following a 5 minute incubation, fluorescence of thapsigargin treated cells is measured. Delta fluorescence values are determined by subtracting baseline fluorescence values from thapsigargin induced fluorescence values.

SUMMARY OF TEST RESULTS

| COMPOUND NO. | Ca$^{+2}$ INFLUX IC$_{50}$ ($\mu$M) | IL-2 PRODUCTION IC$_{50}$ ($\mu$M) Protocol A | Protocol B | ALLOGENEIC CELL TRANSPLANT % | mg/kg | IL-2 PROMOTER IC$_{50}$ ($\mu$M) |
|---|---|---|---|---|---|---|
| 1  | 0.3  | 2    | 6.2   | 38 | 1   | 1.5  |
| 2  | 2.2  | 14   | —     | —  | —   | —    |
| 3  | 17.2 | 38   | 21    | —  | —   | —    |
| 4  | 0.5  | 0.3  | 3.4   | 38 | 0.1 | 0.23 |
| 5  | 0.3  | 1    | 4.2   | 60 | 1   | 1.09 |
| 6  | 14   | 9.2  | >25   | —  | —   | 3.2  |
| 7  | 0.7  | 5    | 9.8   | 49 | 1   | 3    |
| 8  | 2.2  | >20  | 7.4   | —  | —   | —    |
| 9  | 1.1  | 5    | >25   | —  | —   | —    |
| 10 | 4.6  | 27   | >25   | —  | —   | —    |
| 11 | 6.4  | 3    | 20    | —  | —   | —    |
| 12 | 1.2  | 0.3  | 4.5   | 49 | 1   | —    |
| 13 | 0.5  | 0.8  | 8.1   | —  | —   | —    |
| 14 | 29   | 36   | 22    | —  | —   | —    |
| 15 | 0.9  | —    | 9     | —  | —   | —    |
| 16 | 4.5  | —    | >25   | —  | —   | —    |
| 17 | 0.4  | —    | 4.2   | —  | —   | —    |
| 18 | 0.7  | —    | 5.4   | —  | —   | —    |
| 19 | 3.4  | —    | 6.3   | —  | —   | —    |
| 20 | 0.3  | —    | 1.1   | —  | —   | —    |
| 21 | 2.9  | —    | —     | —  | —   | —    |
| 22 | 1.7  | —    | 5.8   | —  | —   | —    |
| 23 | 15.2 | —    | —     | —  | —   | —    |
| 24 | 1.6  | —    | 0.17  | —  | —   | —    |
| 25 | 7.7  | —    | —     | —  | —   | —    |
| 26 | 2.5  | —    | >25   | —  | —   | —    |
| 27 | 1.3  | —    | 5.6   | —  | —   | —    |
| 28 | 0.7  | —    | 4.8   | —  | —   | —    |
| 29 | 2.7  | —    | 1.6   | —  | —   | —    |
| 30 | 1.7  | —    | 5,9   | —  | —   | —    |
| 31 | 3.3  | —    | 2.8   | —  | —   | —    |
| 32 | 1.5  | —    | 8.9   | —  | —   | —    |
| 33 | 1    | —    | 5.3   | —  | —   | —    |
| 34 | 2.4  | —    | 7.7   | —  | —   | —    |
| 35 | 0.7  | —    | —     | —  | —   | —    |
| 36 | 3.3  | —    | 17    | —  | —   | —    |
| 37 | 2.2  | —    | >25   | —  | —   | —    |
| 38 | 2.2  | —    | >25   | —  | —   | —    |
| 39 | 0.7  | —    | 9.5   | —  | —   | —    |
| 40 | 14.4 | —    | >25   | —  | —   | —    |
| 41 | 17.7 | —    | >25   | —  | —   | —    |
| 42 | 1.3  | —    | 2.5   | —  | —   | —    |
| 43 | >45  | —    | >25   | —  | —   | —    |
| 44 | 1.3  | —    | <10   | —  | —   | —    |

The disclosure of all material and documents cited herein is expressly incorporated by reference.

While we have described a number of embodiments of this invention, it is apparent that our basic constructions may be altered to provide other embodiments which utilize the products and methods of this invention. Therefore, it will be appreciated that the scoppe of this invention is to be defined by the appended claims, rather than by the specific embodiments that have been presented herein by way of example.

We claim:
1. A compound of formula (I):

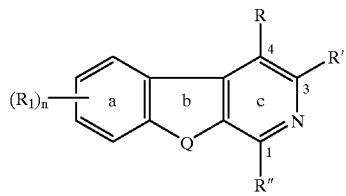

wherein:
Q is selected from the group consisting of N—R$_2$, O or S;
n is an integer selected from the group consisting of 0, 1, 2, 3 and 4;
R is selected from the group consisting of C$_2$–C$_6$ branched or unbranched alkynyl, NR$_3$R$_4$, phenyl substituted with one or more independently selected R$_1$, naphthyl optionally substituted with one or more independently selected $R_1$ and heterocycles selected from the group consisting of benzimidazolyl, imidazolyl, imidazolinoyl, imidazolidinyl, quinolyl, isoquinolyl, indolyl, oxadiazolyl, pyridyl, pyrrolyl, pyrazolyl, pyrazinyl, quinoxolyl, piperidinyl, morpholinyl, thiamorpholinyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazolyl, benzodioxolyl, tetrahydrothiophenyl and sulfolanyl each optionally substituted with one or more independently selected $R_1$;

R' and R" are independently selected from the group consisting of H, halo and $C_1$–$C_3$ alkyl;

each $R_1$ is independently selected from the group consisting of OH, nitro, $NR_3R_4$, $COR_4$, $CO_2R_4$, cyano, halo, $C_3$–$C_8$ cycloalkyl, $C_3$–$C_8$ cycloalkenyl, $C_1$–$C_6$ branched or unbranched alkyl, $C_2$–$C_6$ branched or unbranched alkenyl, $C_2$–$C_6$ branched or unbranched alkynyl, $C_1$–$C_6$ branched or unbranched alkoxy, wherein said cycloalkyl, cycloalkenyl, alkyl, alkenyl, alkynyl or alkoxy may be optionally substituted with one to three substituents (the same or different) independently selected from the group consisting of OH, $NR_3R_4$, $COR_4$, $CO_2R_4$, cyano and halo;

$R_2$ is selected from the group consisting of H, an amino protecting group, $C_1$–$C_6$ branched or unbranched alkyl, $C_2$–$C_6$ branched or unbranched alkenyl, $C_2$–$C_6$ branched or unbranched alkynyl and benzyl;

each $R_3$ is independently selected from the group consisting of H, $C_1$–$C_6$ branched or unbranched alkyl; $C_2$–$C_6$ branched or unbranched alkenyl, $C_2$–$C_6$ branched or unbranched alkynyl, $C_1$–$C_6$ branched or unbranched alkoxy, phenyl and benzyl; and each $R_4$ is independently selected from the group consisting of H, phenyl and $C_1$–$C_6$ branched and unbranched alkyl optionally substituted with phenyl with the proviso that R excludes o-methylphenyl, m-methylphenyl, methoxyphenyl, methylpyridinyl, 1-benzylimidazol-2-yl, N-methyl-piperidin-2-yl, 1-methyl-imidazolyl-2-yl and amino.

2. The compound according to claim 1, wherein R' is H when R is $C_2$–$C_6$ branched or unbranched alkynyl.

3. The compound according to claim 1, with the proviso that R excludes $C_2$–$C_6$ branched or unbranched alkynyl.

4. The compound according to claim 3, wherein R' is H.

5. The compound according to claim 3, wherein R is selected from the group consisting of heterocycles selected from the group consisting of benzimidazolyl, imidazolyl, imidazolinoyl, imidazolidinyl, quinolyl, isoquinolyl, indolyl, oxadiazolyl, pyridyl, pyrrolyl, pyrazolyl, pyrazinyl, quinoxolyl, piperidinyl, morpholinyl, thiamorpholinyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazolyl, benzodioxolyl and tetrahydrothiophenyl; $C_3$–$C_8$ cycloalkyl, and phenyl, wherein said heterocycle, or phenyl is substituted with one to three independently selected $R_1$.

6. The compounds according to claim 5, wherein R is selected from the group consisting of heterocycles selected from the group consisting of imidazolyl, imidazolinoyl, imidazolidinyl, oxadiazolyl, pyridyl, pyrrolyl, pyrazolyl, pyrazinyl, piperidinyl, morpholinyl, thiamorpholinyl, thienyl, triazolyl, thiazolyl, tetrazolyl, thiazolidinyl, thiamorpholinyl sulfone, oxopiperidinyl, oxopyrroldinyl, isoxazolyl, tetrahydropyranyl, tetrahydrofuranyl, thiadiazolyl, tetrahydrothiophenyl and sulfolanyl, and phenyl, wherein said heterocycle and phenyl are substituted with one or two groups independently selected from $C_1$–$C_3$ alkoxy, $C_1$–$C_3$ alkyl and $C_1$–$C_3$ fully or partially halogenated alkyl.

7. The compound according to claim 1, wherein:

Q is N—$R_2$;

n is 0, 1 or 2;

R is selected from the group consisting of heterocycles selected from the group consisting of benzimidazolyl, imidazolyl, imidazolinoyl, imidazolidinyl, quinolyl, isoquinolyl, indolyl, oxadiazolyl, pyridyl, pyrrolyl, pyrazolyl, pyrazinyl, quinoxolyl, piperidinyl, morpholinyl, thiamorpholinyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazolyl, benzodioxolyl, tetrahydrothiophenyl and sulfolanyl; and phenyl, wherein said heterocycle and phenyl is substituted with one or two groups independently selected from $C_1$–$C_3$ alkoxy, $C_1$–$C_3$ alkyl and $C_1$–$C_3$ fully or partially halogenated alkyl;

R' is H;

R" is selected from H and methyl;

$R_1$ is selected from the group consisting of OH, amino, halo, $C_1$–$C_3$ alkoxy, $C_1$–$C_3$ alkyl and $C_1$–$C_3$ halogenated alkyl; and $R_2$ is selected from the group consisting of H, $C_1$–$C_3$ alkyl optionally substituted with phenyl.

8. The compounds according to claim 7, wherein:

n is 0 or 1;

R is selected from the group consisting of oxadiazolyl, thienyl, thiazolyl (wherein said oxadiazolyl, thienyl, and thiazolyl are optionally substituted with one or two groups independently selected from $C_1$–$C_3$ alkoxy, $C_1$–$C_3$ alkyl and $C_1$–$C_3$ fully or partially halogenated alkyl) and phenyl substituted with one or two groups independently selected from $C_1$–$C_3$ alkoxy, $C_1$–$C_3$ alkyl and $C_1$–$C_3$ fully or partially alkyl;

R' and R" are both H;

$R_1$ is selected from the group consisting of halo and $C_1$–$C_3$ alkyl; and $R_2$ is selected from the group consisting of H and $C_1$–$C_3$ alkyl optionally substituted with phenyl.

9. A compound selected from the group consisting of 4-(p-methoxyphenyl)-β-carboline, 4-(p-methylphenyl)-β-carboline, 4-(p-trifluoromethylphenyl)-β-carboline, 4-(p-isopropylphenyl)-β-carboline and 4-(p-dimethylaminophenyl)-β-carboline.

10. A pharmaceutical composition comprising the compounds according to any one of claims 1–9 and a pharmaceutically acceptable carrier or adjuvant.

11. A method for treating an IL-2 mediated immune disorder comprising the step of administering to a patient in need thereof a therapeutically effective amount of a pharmaceutical composition comprising a compound of formula (I):

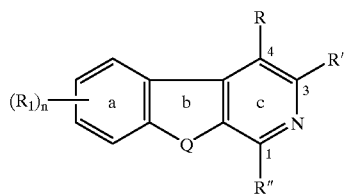

wherein:
Q is selected from the group consisting of N—$R_2$, O or S;
n is an integer selected from the group consisting of 0, 1, 2, 3 and 4;
R is selected from the group consisting of $COR_4$, $CO_2R_4$, $C_3$–$C_8$ cycloalkyl, $C_1$–$C_6$ branched or unbranched alkyl, $C_2$–$C_6$ branched or unbranched alkenyl, $C_2$–$C_6$ branched or unbranched alkynyl, $C_1$–$C_6$ branched or unbranched alkoxy, halogen, $NR_3R_4$, phenyl optionally substituted with one or more independently selected $R_1$, benzyl optionally substituted with one or more independently selected $R_1$, naphthyl optionally substituted with one or more independently selected $R_1$ and heterocycles selected from the group consisting of benzimidazolyl, imidazolyl, imidazolinoyl, imidazolidinyl, quinolyl, isoquinolyl, indolyl, oxadiazolyl, pyridyl, pyrrolyl, pyrrolinyl, pyrazolyl, pyrazinyl, quinoxolyl, piperidinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazolyl, benzodioxolyl, tetrahydrothiophenyl and sulfolanyl; said heterocycles optionally substituted with one or more independently selected $R_1$;
R' and R" are independently selected from the group consisting of H, halo and $C_1$–$C_3$ alkyl;
each $R_1$ is independently selected from the group consisting of OH, nitro, $NR_3R_4$, $COR_4$, $CO_2R_4$, cyano, halo, $C_3$–$C_8$ cycloalkyl, $C_3$–$C_8$ cycloalkenyl, $C_1$–$C_6$ branched or unbranched alkyl, $C_2$–$C_6$ branched or unbranched alkenyl, $C_2$–$C_6$ branched or unbranched alkynyl, $C_1$–$C_6$ branched or unbranched alkoxy, wherein said cycloalkyl, cycloalkenyl, alkyl, alkenyl, alkynyl or alkoxy may be optionally substituted with one to three substituents (the same or different) independently selected from the group consisting of OH, $NR_3R_4$, $COR_4$, $CO_2R_4$, cyano and halo;
$R_2$ is selected from the group consisting of H, an amino protecting group, $C_1$–$C_6$ branched or unbranched alkyl, $C_2$–$C_6$ branched or unbranched alkenyl, $C_2$–$C_6$ branched or unbranched alkynyl and benzyl;
each $R_3$ is independently selected from the group consisting of H, $C_1$–$C_6$ branched or unbranched alkyl; $C_2$–$C_6$ branched or unbranched alkenyl, $C_2$–$C_6$ branched or unbranched alkynyl, $C_1$–$C_6$ branched or unbranched alkoxy, phenyl and benzyl; and
each $R_4$ is independently selected from the group consisting of H, phenyl and $C_1$–$C_6$ branched and unbranched alkyl optionally substituted with phenyl and a pharmaceutically acceptable carrier or adjuvant.

12. The method according to claim 11, wherein the immune disorder is selected from the group consisting of acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, organ transplant rejection and lupus erythematosus.

13. The method according to claim 11, wherein the immune disorder is rheumatoid arthritis, multiple sclerosis or inflammatory bowel disease.

14. A method for reducing immunoglobulin synthesis, inhibiting IL-2 production or inhibiting $Ca^{+2}$ influx comprising the step of administering to a patient in need thereof a immunoglobulin synthesis reducing, IL-2 production inhibiting or calcium influx inhibiting amount of a pharmaceutical composition comprising a compound of formula (I)

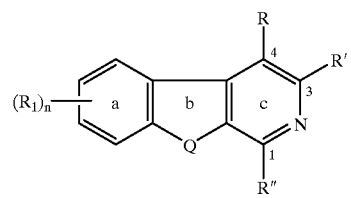

wherein:
Q is selected from the group consisting of N—$R_2$, O or S;
n is an integer selected from the group consisting of 0, 1, 2, 3 and 4;
R is selected from the group consisting of $COR_4$, $CO_2R_4$, $C_3$–$C_8$ cycloalkyl, $C_1$–$C_6$ branched or unbranched alkyl, $C_2$–$C_6$ branched or unbranched alkenyl, $C_2$–$C_6$ branched or unbranched alkynyl, $C_1$–$C_6$ branched or unbranched alkoxy, halogen, $NR_3R_4$, phenyl optionally substituted with one or more independently selected $R_1$, benzyl optionally substituted with one or more independently selected $R_1$, naphthyl optionally substituted with one or more independently selected $R_1$ and heterocycles selected from the group consisting of benzimidazolyl, imidazolyl, imidazolinoyl, imidazolidinyl, quinolyl, isoquinolyl, indolyl, oxadiazolyl, pyridyl, pyrrolyl, pyrrolinyl, pyrazolyl, pyrazinyl, quinoxolyl, piperidinyl, morpholinyl, thianorpholinyl, furyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazolyl, benzodioxolyl, tetrahydrothiophenyl and sulfolanyl; said heterocycles optionally substituted with one or more independently selected $R_1$;
R' and R" are independently selected from the group consisting of H, halo and $C_1$–$C_3$ alkyl;
each $R_1$ is independently selected from the group consisting of OH, nitro, $NR_3R_4$, $COR_4$, $CO_2R_4$, cyano, halo, $C_3$–$C_8$ cycloalkyl, $C_3$–$C_8$ cycloalkenyl, $C_1$–$C_6$ branched or unbranched alkyl, $C_2$–$C_6$ branched or unbranched alkenyl, $C_2$–$C_6$ branched or unbranched alkynyl, $C_1$–$C_6$ branched or unbranched alkoxy, wherein said cycloalkyl, cycloalkenyl, alkyl, alkenyl, alkynyl or alkoxy may be optionally substituted with one to three substituents (the same or different) independently selected from the group consisting of OH, $NR_3R_4$, $COR_4$, $CO_2R_4$, cyano and halo;
$R_2$ is selected from the group consisting of H, an amino protecting group, $C_1$–$C_6$ branched or unbranched alkyl, $C_2$–$C_6$ branched or unbranched alkenyl, $C_2$–$C_6$ branched or unbranched alkynyl and benzyl;

each $R_3$ is independently selected from the group consisting of H, $C_1$–$C_6$ branched or unbranched alkyl; $C_2$–$C_6$ branched or unbranched alkenyl, $C_2$–$C_6$ branched or unbranched alkynyl, $C_1$–$C_6$ branched or unbranched alkoxy, phenyl and benzyl; and each $R_4$ is independently selected from the group consisting of H, phenyl and $C_1$–$C_6$ branched and unbranched alkyl optionally substituted with phenyl and a pharmaceutically acceptable carrier or adjuvant.

15. A method for reducing T-cell proliferation comprising the step of administering to a patient in need thereof a T-cell proliferation reducing amount of a pharmaceutical composition comprising a compound of formula (I):

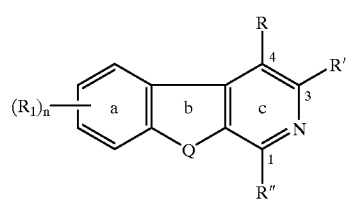

(I)

wherein:

Q is selected from the group consisting of N—$R_2$, O or S;

n is an integer selected from the group consisting of 0, 1, 2, 3 and 4;

R is selected from the group consisting of $COR_4$, $C_2R_4$, $C_3$–$C_8$ cycloalkyl, $C_1$–$C_6$ branched or unbranched alkyl, $C_2$–$C_6$ branched or unbranched alkenyl, $C_2$–$C_6$ branched or unbranched alkynyl, $C_1$–$C_6$ branched or unbranched alkoxy, halogen, $NR_3R_4$, phenyl optionally substituted with one or more independently selected $R_1$, benzyl optionally substituted with one or more independently selected $R_1$, naphthyl optionally substituted with one or more independently selected $R_1$ and heterocycles selected from the group consisting of benzimidazolyl, imidazolyl, imidazolinoyl imidazolidinyl, quinolyl, isoquinolyl, indolyl, oxadiazolyl, pyridyl, pyrrolyl, pyrrolinyl, pyrazolyl, pyrazinyl, quinoxolyl, piperidinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazolyl, benzodioxolyl, tetrahydrothiophenyl and sulfolanyl: said heterocycles optionally substituted with one or more independently selected $R_1$;

R' and R" are independently selected from the group consisting of H, halo and $C_1$–$C_3$ alkyl;

each $R_1$ is independently selected from the group consisting of OH, nitro, $NR_3R_4$, $COR_4$, $CO_2R_4$, cyano, halo, $C_3$–$C_8$ cycloalkyl, $C_3$–$C_8$ cycloalkenyl, $C_1$–$C_6$ branched or unbranched alkyl, $C_2$–$C_6$ branched or unbranched alkenyl, $C_2$–$C_6$ branched or unbranched alkynyl, $C_1$–$C_6$ branched or unbranched alkoxy, wherein said cycloalkyl, cycloalkenyl, alkyl, alkenyl, alkynyl or alkoxy may be optionally substituted with one to three substituents (the same or different) independently selected from the group consisting of OH, $NR_3R_4$, $COR_4$, $CO_2R_4$, cyano and halo;

$R_2$ is selected from the group consisting of H, an amino protecting group, $C_1$–$C_6$ branched or unbranched alkyl, $C_2$–$C_6$ branched or unbranched alkenyl, $C_2$–$C_6$ branched or unbranched alkynyl and benzyl;

each $R_3$ is independently selected from the group consisting of H, $C_1$–$C_6$ branched or unbranched alkyl; $C_2$–$C_6$ branched or unbranched alkenyl, $C_2$–$C_6$ branched or unbranched alkynyl, $C_1$–$C_6$ branched or unbranched alkoxy, phenyl and benzyl; and each $R_4$ is independently selected from the group consisting of H, phenyl and $C_1$–$C_6$ branched and unbranched alkyl optionally substituted with phenyl and a pharmaceutically acceptable carrier or adjuvant.

16. A method for preparing a compound of formula (I) of claim 1 comprising the steps of:
   (a) reacting a substituted indole with trans β-nitrostyrene or trans o-substituted, m-substituted or p-substituted-β-nitrostyrene to give a substituted 3-(2-nitro)ethyl indole;
   (b) reducing the substituted 3-(2-nitro)ethyl indole in the presence of a catalyst to produce an 3-(2-amino)ethyl indole;
   (c) treating the 3-(2-amino)ethyl indole with 1-tosyl-3,4,4-trimethylimidazolidine to produce a tetrahydro-β-carboline derivative; and
   (d) aromatizing the tetrahydro-β-carboline derivative to produce the compound of formula (I).

17. A method for producing a compound of formula (I) of claim 1 comprising the steps of:
   (a) reacting a 3-(2-amino)ethyl indole derivative with diethyl ethoxymethylenemalonate to produce a coupled malonate derivative;
   (b) treating the coupled malonate derivative with TFA to produce a 3,4-dihydro-β-carboline derivative; and
   (c) aromatizing the 3,4-dihydro-β-carboline derivative to produce the compound of formula (I).

18. A method for producing a compound of formula (I) of claim 1 comprising the steps of:
   (a) oxidizing a substituted tetrahydro-β-carboline in which the c-ring is N-protected to produce a 4-oxo derivative;
   (b) protecting the indole nitrogen with a nitrogen protecting group to produce an N,N-di-protected 4-oxo derivative;
   (c) treating the N,N-di-protected 4-oxo derivative with a Grignard reagent to produce a 4-substituted, 4-hydroxy N,N-di-protected derivative; and
   (d) reacting the 4-substituted, 4-hydroxy N,N-di-protected derivative with TFA to produce a compound of formula (I).

19. The method for treating an IL-2 mediated immune disorder according to claim 11, wherein the compound of formula (I) has the following proviso:

R excludes $C_1$–$C_6$ branched or unbranched alkyl, $C_2$–$C_6$ branched or unbranched alkenyl, $C_2$–$C_6$ branched or unbranched alkynyl, $C_1$–$C_6$ branched or unbranched alkoxy, $COR_4$ and $CO_2R_4$.

20. The method for reducing immunoglobulin synthesis, inhibiting IL-2 production or inhibiting $Ca^{+2}$ influx according to claim 14 wherein the compound of formula (I) has the following proviso:

R excludes $C_1$–$C_6$ branched or unbranched alkyl, $C_2$–$C_6$ branched or unbranched alkenyl, $C_2$–$C_6$ branched or unbranched alkynyl, $C_1$–$C_6$ branched or unbranched alkoxy, $COR_4$ and $CO_2R_4$.

21. The method for reducing T-cell proliferation according to claim 15 wherein the compound of formula (I) has the following proviso:

R excludes $C_1$–$C_6$ branched or unbranched alkyl, $C_2$–$C_6$ branched or unbranched alkenyl, $C_2$–$C_6$ branched or unbranched alkynyl, $C_1$–$C_6$ branched or unbranched alkoxy, $COR_4$ and $CO_2R_4$.

22. The method for treating an IL-2 mediated immune disorder according to claim 11, wherein R of the compound of formula (I) is selected from the group consisting of:

heterocycles selected from the group consisting of imidazolyl, imidazolinoyl, imidazolidinyl, oxadiazolyl, pyridyl, pyrrolyl, pyrrolinyl, pyrazolyl, pyrazinyl, piperidinyl, morpholinyl, thiamorpholinyl, furyl, thienyl, triazolyl, thiazolyl, tetrazolyl, thiazolidinyl, thiamorpholinyl sulfone, oxopiperidinyl, oxopyrroldinyl, isoxazolyl, tetrahydropyranyl, tetrahydrofuranyl, thiadiazolyl, tetrahydrothiophenyl and sulfolanyl, benzyl and phenyl, wherein said heterocycle, benzyl and phenyl are substituted with one or two groups independently selected from $C_1$–$C_3$ alkoxy, $C_1$–$C_3$ alkyl and $C_1$–$C_3$ fully or partially halogenated alkyl.

23. The method for reducing immunoglobulin synthesis, inhibiting IL-2 production or inhibiting $Ca^{+2}$ influx according to claim 14 wherein R of the compound of formula (I) is selected from the group consisting of:

heterocycles selected from the group consisting of imidazolyl, imidazolinoyl, imidazolidinyl, oxadiazolyl, pyridyl, pyrrolyl, pyrrolinyl, pyrazolyl, pyrazinyl, piperidinyl, morpholinyl, thiamorpholinyl, furyl, thienyl, triazolyl, thiazolyl, tetrazolyl, thiazolidinyl, thiamorpholinyl sulfone, oxopiperidinyl, oxopyrroldinyl, isoxazolyl, tetrahydropyranyl, tetrahydrofuranyl, thiadiazolyl, tetrahydrothiophenyl and sulfolanyl, benzyl and phenyl, wherein said heterocycle, benzyl and phenyl are substituted with one or two groups independently selected from $C_1$–$C_3$ alkoxy, $C_1$–$C_3$ alkyl and $C_1$–$C_3$ fully or partially halogenated alkyl.

24. The method for reducing T-cell proliferation according to claim 15 wherein R of the compound of formula (I) is selected from the group consisting of:

heterocycles selected from the group consisting of imidazolyl, imidazolinoyl, imidazolidinyl, oxadiazolyl, pyridyl, pyrrolyl, pyrrolinyl, pyrazolyl, pyrazinyl, piperidinyl, morpholinyl, thiamorpholinyl, furyl, thienyl, triazolyl, thiazolyl, tetrazolyl, thiazolidinyl, thiamorpholinyl sulfone, oxopiperidinyl, oxopyrroldinyl, isoxazolyl, tetrahydropyranyl, tetrahydrofuranyl, thiadiazolyl, tetrahydrothiophenyl and sulfolanyl, benzyl and phenyl, wherein said heterocycle, benzyl and phenyl are substituted with one or two groups independently selected from $C_1$–$C_3$ alkoxy, $C_1$–$C_3$ alkyl and $C_1$–$C_3$ fully or partially halogenated alkyl.

\* \* \* \* \*